United States Patent
Yao et al.

(10) Patent No.: US 6,409,670 B1
(45) Date of Patent: Jun. 25, 2002

(54) HIGH SAMPLE RATE DOPPLER ULTRASOUND SYSTEM

(75) Inventors: Lin Xin Yao; Gan Yao, both of Bellevue, WA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/559,492

(22) Filed: Apr. 27, 2000

(51) Int. Cl.$^7$ ................................................. A61B 8/06
(52) U.S. Cl. ....................................................... 600/453
(58) Field of Search ................................ 600/437, 440, 600/441, 443, 447, 453–457, 465; 73/625, 626; 367/7, 11

(56) References Cited

U.S. PATENT DOCUMENTS 5,501,224 A * 3/1996 Shiki .......................... 600/456

* cited by examiner

Primary Examiner—Marvin M. Lateef
Assistant Examiner—Ali M. Imam (57) ABSTRACT

A method for receiving Doppler ultra sound signals at a high sample rate, at greater depths and from a large range gate size by increasing the length of time during which echoes can be received with respect to the time required to transmit the Doppler pulses that cause the echo signals to be created. According to a first embodiment of the invention, a Doppler pulse is transmitted for a time equal to the time required for an ultrasonic sound wave to travel from a transducer to a top of a range gate and back. Echo signals created in response to the long Doppler pulse are received for a time equal to the transmit time plus the time required for an ultrasonic sound wave to travel from the top of the range gate to a bottom of the range gate and back to the top of the range gate. In accordance with another aspect of the invention, each transducer element transmits a phase-shifted Doppler pulse, wherein the phase-shift is selected according to the time required for an ultrasonic sound wave to travel from the transducer element to a desired focal point. By simultaneously transmitting the phase-shifted Doppler pulses, the pulses arrive at different times at the focal point and constructively add. Echo signals created in response to the sum of the phase-shifted Doppler pulses can be sampled at substantially any rate to analyze the moving blood flow in the area of tissue defined by a range gat.

7 Claims, 9 Drawing Sheets

HIGH SAMPLE RATE DOPPLER
ULTRASOUND SYSTEM

FIELD OF THE INVENTION

The present invention relates to medical imaging systems in general, and in particular to Doppler untrasound imaging systems.

BACKGROUND OF THE INVENTION

Ultrasound imaging is a commonly used technique for non-invasively imaging a patient's internal tissue and organs as well as for analyzing which ultrasonic sound waves travel in the body. The maximum depth of tissue that can be analyzed with Doppler pulses is limited to one half of the distance that a Doppler pulse can travel between successive pulses. For example, at a PRF of 40 KHz, the maximum depth of tissue that can be analyzed by Doppler pulses that travel at 1.54 mm/$\mu$sec is 19.25 mm. However, to accurately analyze blood flow within the heart, it is often necessary to analyze blood flow at depths of 80 to 100 mm.

Another approach used in conventional pulsed Doppler systems is called multi-pulse Doppler, where Doppler pulses are periodically transmitted and echo signals are received between transmission time. This approach products high sample rate echo signals at greater tissue depths. However, the range gate size is limited because of the time required to transmit the Doppler pulses. For example, the 19.25 mm range gate size for Doppler pulses transmitted at 40 KHz is often limited to 5 mm in practice due to the delays inherent in transmitting the pulses.

To increase the amount of echo data that can be used to analyze blood flow, many ultrasound systems transmit continuous wave (CW) Doppler signals into the body. Analog Doppler systems do allow high sample rates, good depths and large range gate sizes. However, such systems generally require a separate analog beamformer to receive the corresponding echo signals, which increases the cost and complexity of the ultrasound system. Digital CW beamformers have not generally been successful because the difference in magnitude between the Doppler pulses transmitted into the patient and the relatively weak echo signals received is too great for the digital beamformer to interpret accurately.

Given these problems associated with Doppler ultrasound imaging, there is a need for a method of increasing the amount of echo data that can be used to analyze blood flow without the use of additional hardware or sacrificing accuracy.

SUMMARY OF THE INVENTION

To address the limitations discussed above, the present invention is a method for obtaining Doppler echo data at relatively deep positions in the body, at high sample rates, and with a large range gate size without an analog beamformer.

According to a first embodiment of the invention, a Doppler pulse is transmitted for a time equal to the time required for an ultrasonic sound wave to travel from an ultrasound transducer to a point in the tissue defined by a top of the range gate and back. Following the transmission of this long Doppler pulse, the ultrasound system receives echo signals for a time equal to the time required for an ultrasonic sound wave to travel from the ultrasound transducer to the top of the range and back plus the time required for the ultrasonic sound wave to travel from the top of the range gate to a point in the tissue defined by a bottom of the range gate and back to the top of the range gate. The received echo signals can be sampled at virtually any rate in order to provide accurate Doppler analysis of the blood flowing in the area of tissue defined by the range gate.

In accordance with another aspect of the present invention, the amount of echo data that can be analyzed and hence the size of the range gate is increased by compensating for the various delay times associated with the position of the different transducer elements with respect to a focal point of a Doppler pulse. First, the time required for an ultrasonic sound wave to travel from each transducer element to a focal point of the Doppler pulse is calculated. This value is then converted to a phase delay of the Doppler pulse transmitted from each element. The phase of the Doppler pulse transmitted from each transducer element is then adjusted such that the phase-adjusted Doppler pulses will add constructively within an area of tissue defined by the range gate when simultaneously transmitted. By transmitting all the Doppler pulses simultaneously, the echo signals that originate within the range gate can be received for a longer period of time. The received echo signals can be sampled at virtually any rate to more accurately analyze moving blood flow.

DETAILED DESCRIPTION OF THE PREFERRED EMBODIMENT

The present invention is a method of receiving high sample rate echo signals from greater depths and from greater range gate sizes by increasing the receive time of ultrasound echo signals.

Figure 1:
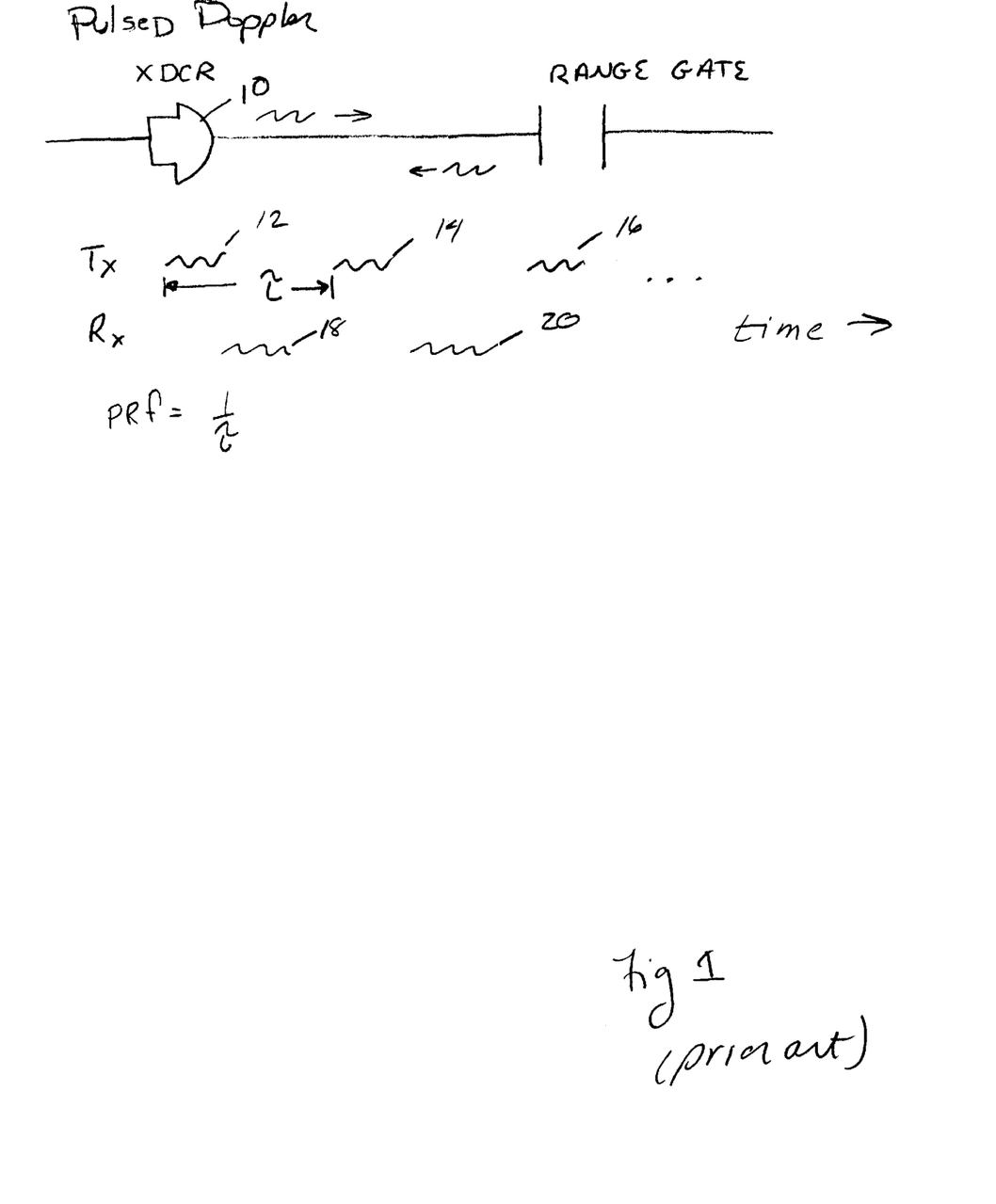
FIG. 1 illustrates how digitally pulsed Doppler ultrasound imaging is limited by the speed of sound in the body.

A conventional method of analyzing blood flow using pulsed Doppler ultrasound is illustrated in FIG. 1. In a pulsed Doppler system, an ultrasound transducer 10 transmits a series of Doppler pulses 12, 14, 16 . . . into the patient.

Each pulse is separated by a time interval τ. Between each of the pulse transmissions, the ultrasound system receives echo signals 18, 20 . . . . Because the echo signals cannot be received while the transducer 10 is transmitting, the size of the range gate from which the echo signals can be received is limited to one half of the distance that the sound waves can travel between successive transmit pulses. As indicated above, this limited depth is generally insufficient to analyze many portions of a patient's heart muscle, which may be 70–100 mm below the ultrasound transducer.

Figure 2:
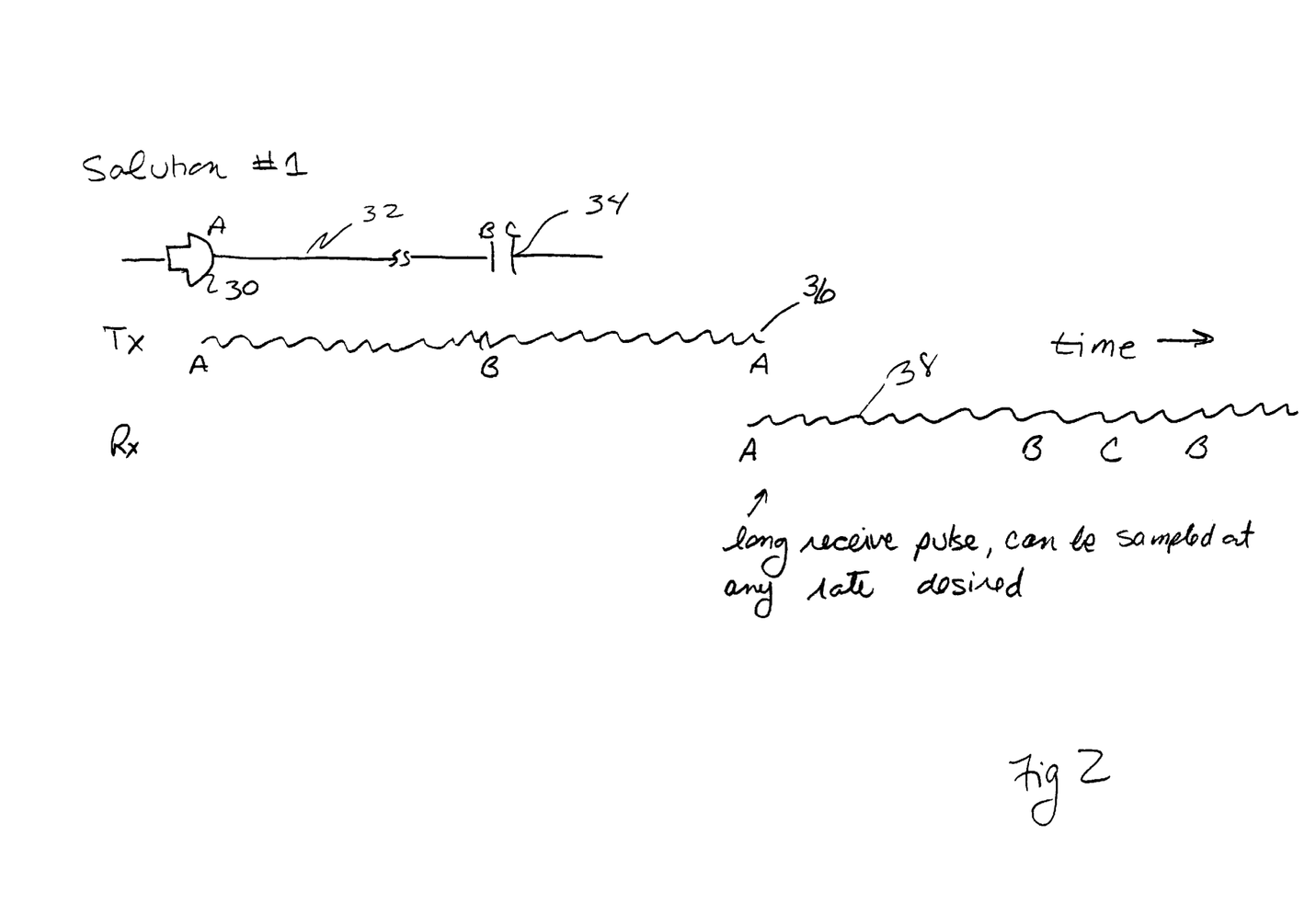
FIG. 2 illustrates a method of increasing the receive time of a Doppler ultrasound signal according to a first embodiment of the invention.

FIG. 2 illustrates a first method of increasing the receive time of an ultrasound echo signal according to a first embodiment of the present invention. A transducer 30 is located at a position A and transmits Doppler pulses along a beam line 32. A user positions a range gate 34 at a position along the beam line. The range gate defines an area of tissue from which the echo signals are to be received in order to analyze the direction and velocity of blood flow. The range gate 34 has a top located at a position B and a bottom of the range gate located at a position C.

To increase the depth from which echo signals can be received, the transducer transmits a Doppler pulse having a duration equal to the time required for an ultrasonic sound wave to travel from the transducer, located at position A, to the top of the range gate located at position B and back to the transducer at position A. This time can generally be estimated based on input from the user regarding the desired depth at which the range gate is to be placed and the known speed of the ultrasonic sound waves in the patient (generally estimated at 1.54 mm per microsecond). After the long Doppler ultrasound pulse 36 has been transmitted, the ultrasound system receives echo signals 38 for a time that is equal to the time required for an ultrasonic sound wave to travel from the transducer 30 located at position A, to the top of the range gate located at position B, to the bottom of the range gate located at position C, and back to the transducer at position A. This length of time again can be estimated from the user supplied depth and size of the range gate and an estimate of the speed of ultrasonic sound waves in the patient. The received echo signals 38 can be sampled at virtually any rate in order to accurately analyze moving blood flow within the area of tissue defined by the position and size of the range gate 34.

In the example shown in FIG. 2, the echo signals can be sampled at a high rate over a large range gate size and the depth from which the echo signals are received is increased. However, echo signals cannot be received during the transmit time and therefore the power spectrum must be estimated using only the data received using autocorrelation or other statistical techniques which require increased processing power.

Figure 3:
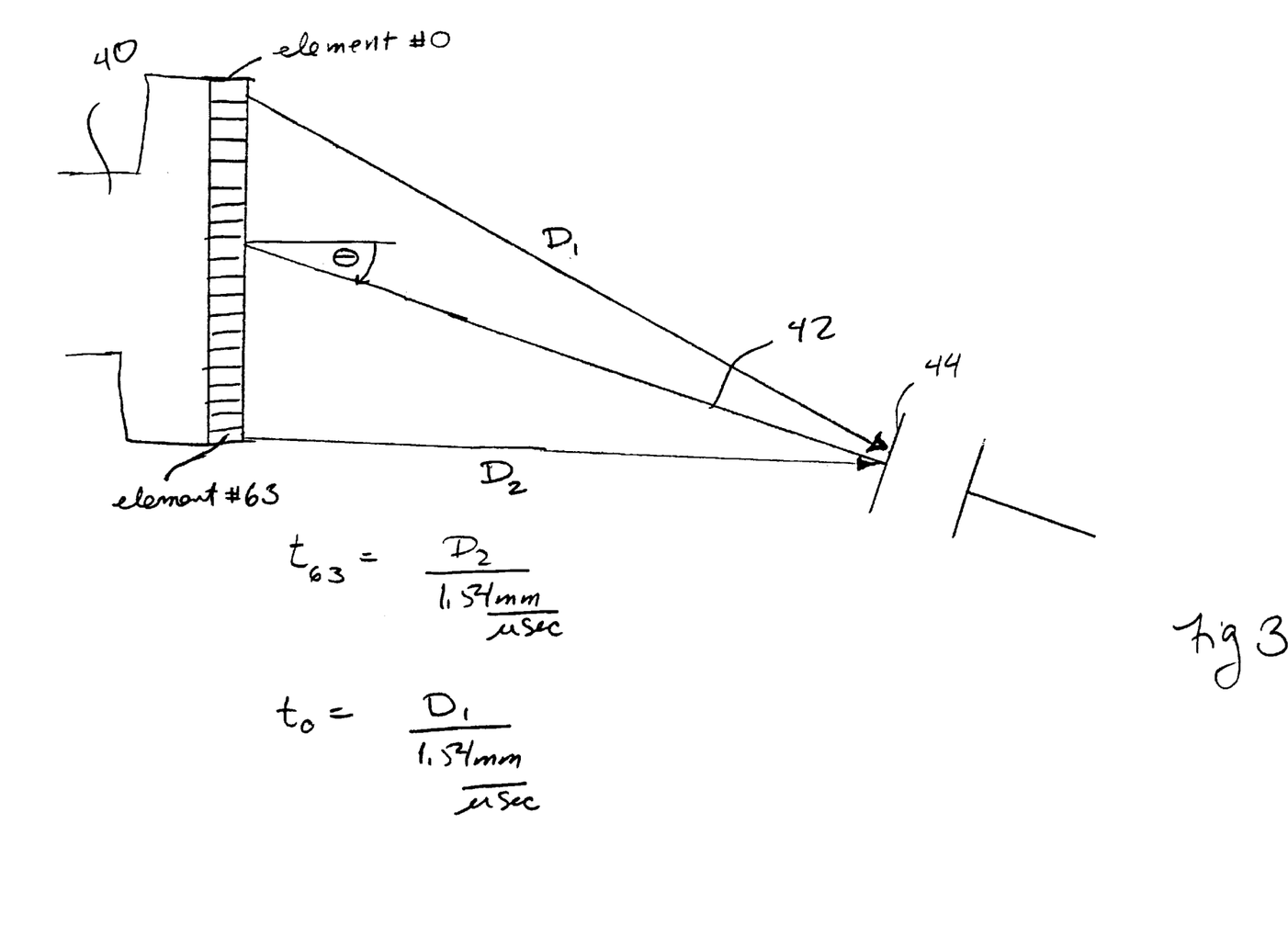
FIG. 3 illustrates differences in the round trip travel time of ultrasound signals transmitted from different transducer elements based on their position with respect to a focal point of a Doppler pulse.

FIG. 3 illustrates the reason why the range gate size is limited in conventional multi-pulse Doppler ultrasound systems. A transducer 40 typically comprises 64, 128 or 256 individual piezoelectric crystal elements that transmit ultrasound pulses into the patient and convert received echoes into electrical signals that are analyzed by processors in the ultrasound system. When ultrasound pulses are transmitted along a beam line 42, the distance between each element and a focal point of the pulses differ. In the example shown, a range gate 44 is positioned along the beam line 42 and marks the focal point of the Doppler pulses. The beam line 42 is oriented at an angle theta with respect to the center of the transducer 40. An ultrasound pulse originating from element #0 on the transducer must travel a distance $D_1$ to the focal point. Similarly, an ultrasound pulse originating from element #63 must travel a distance $D_2$ to the focal point.

Therefore, in order to focus the Doppler pulses from each of these two elements such that they arrive at the focal point at the same time, each of the transducer elements transmits a Doppler pulse at a slightly different time.

Figure 4:
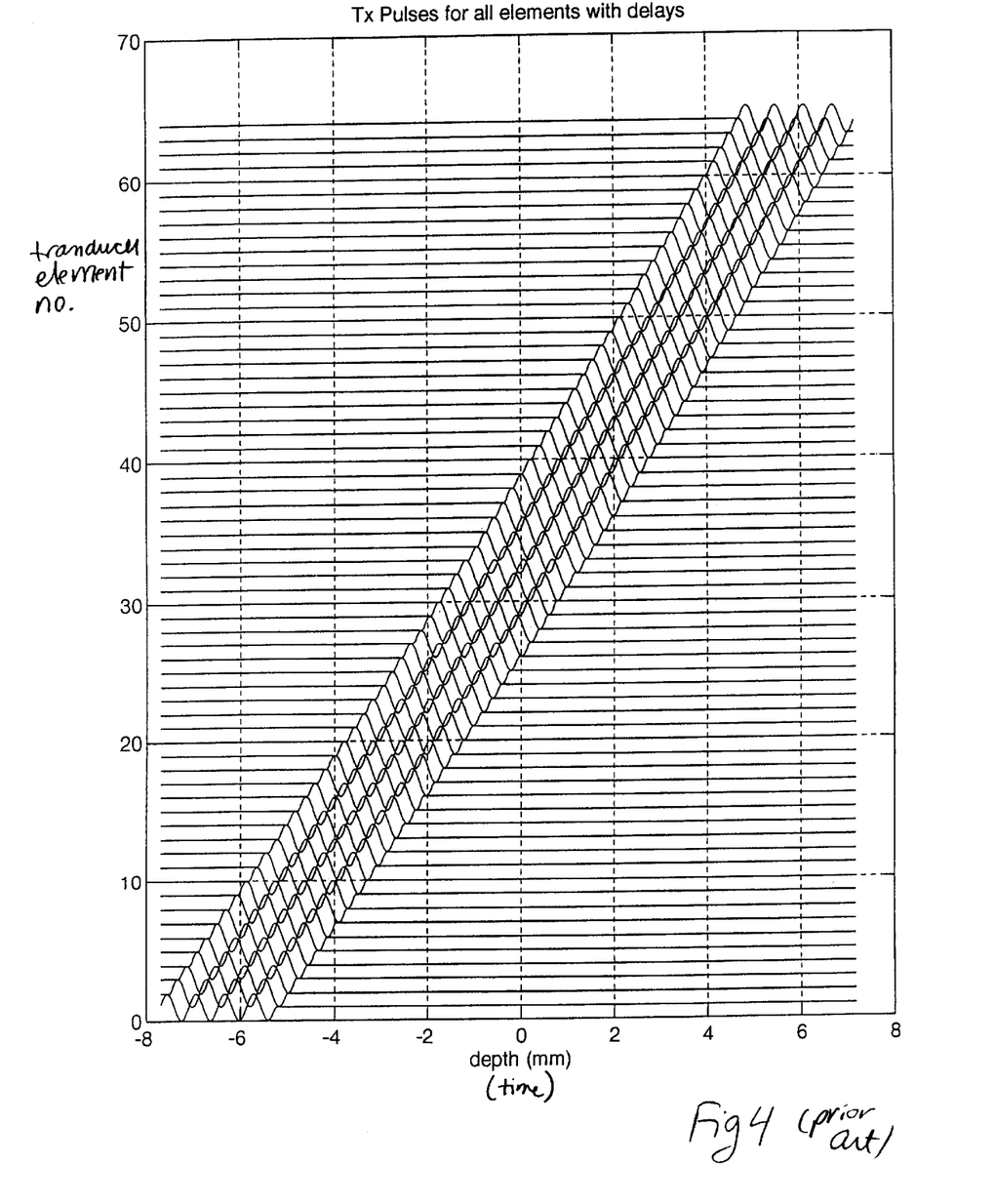
FIG. 4 illustrates a conventional method of transmitting Doppler ultrasound pulses from a transducer having elements that are located at different distances from a focal point of the Doppler pulse.

FIG. 4 illustrates the conventional method of transmitting Doppler pulses from a number of transducer elements in order to compensate for the delays associated with the varying distances between each transducer element and the focal point. Transducer element #0, which is the furthest away from the focal point, transmits a Doppler pulse followed by transducer element #1, and so forth, until transducer element #63, which is the closest element to the focal point.

Figure 5A:
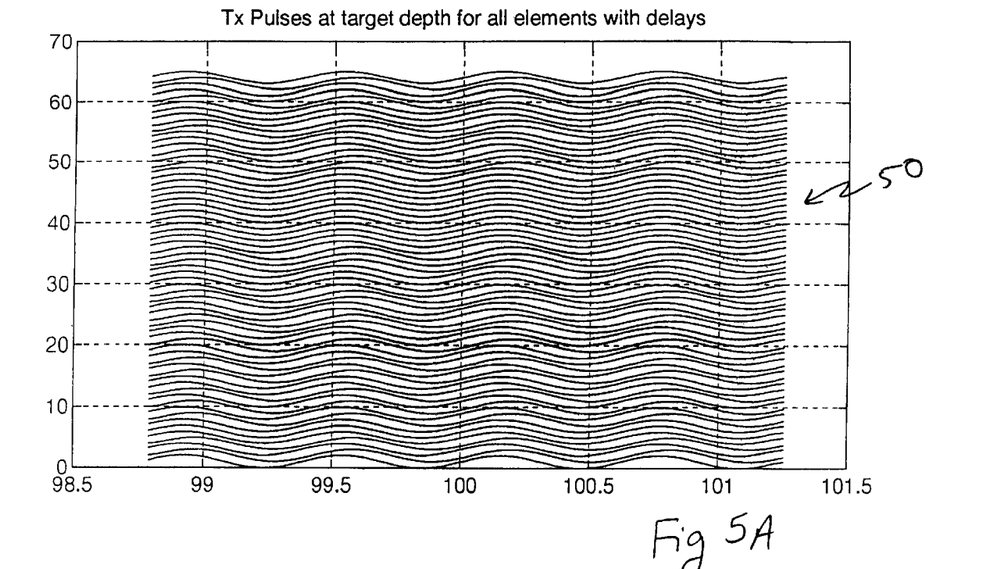
FIGS. 5A and 5B illustrate the constructive effect of the Doppler ultrasound pulses transmitted in the manner shown in FIG. 4.
Figure 5B:
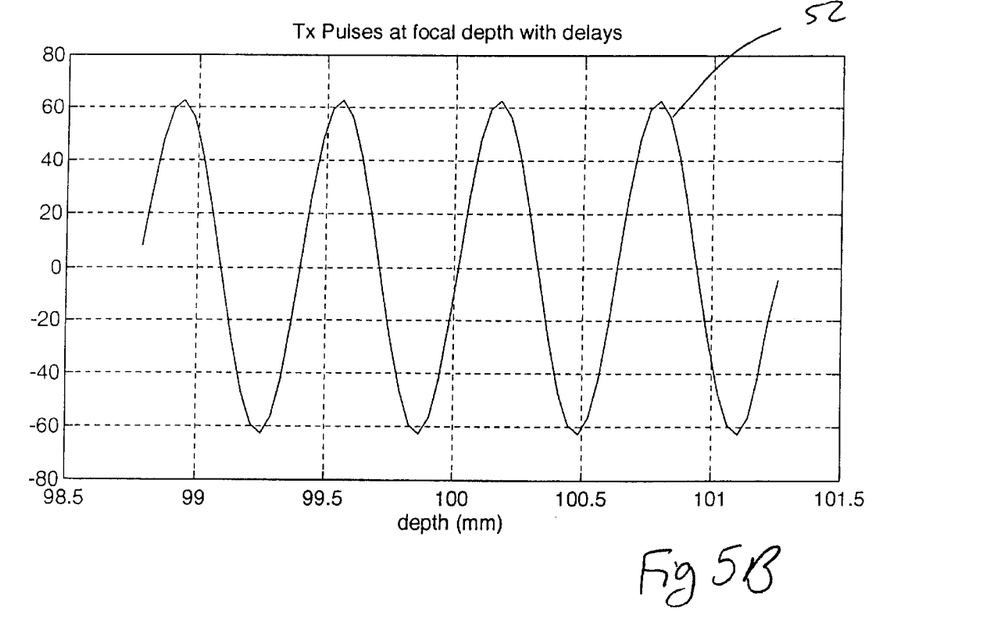

FIGS. 5A and 5B illustrate the combined effect of the staggered pulse transmissions from each of the transducer elements. If timed correctly, each of the Doppler pulses 50 transmitted from the transducer elements arrives at the focal point at substantially the same time as shown in FIG. 5A and constructively add to form a combined pulse 52 at the focal point as shown in FIG. 5B.

The problem with the traditional method of compensating for the various transmission delays as illustrated in FIGS. 4, 5A and 5B is that the time between the first transmission and the last transmission is significantly longer than the duration of the individual Doppler pulses themselves. Therefore, the majority of time between Doppler pulse transmissions is spent transmitting the Doppler pulses in a manner that ensures they arrive at the focal point at the same time. The echo signals generated in response to the combined pulse 52 can only be received for a time equal to the duration of the combined pulse 52 before the next set of Doppler pulses are transmitted thereby limiting the size of the range gate.

To increase the time during which echo signals can be received compared to the transmit time and therefore increase the size of the range gate, an alternative embodiment of the present invention compensates for the varying distances by adjusting the phase of the Doppler pulse transmitted from each element.

Figure 6:
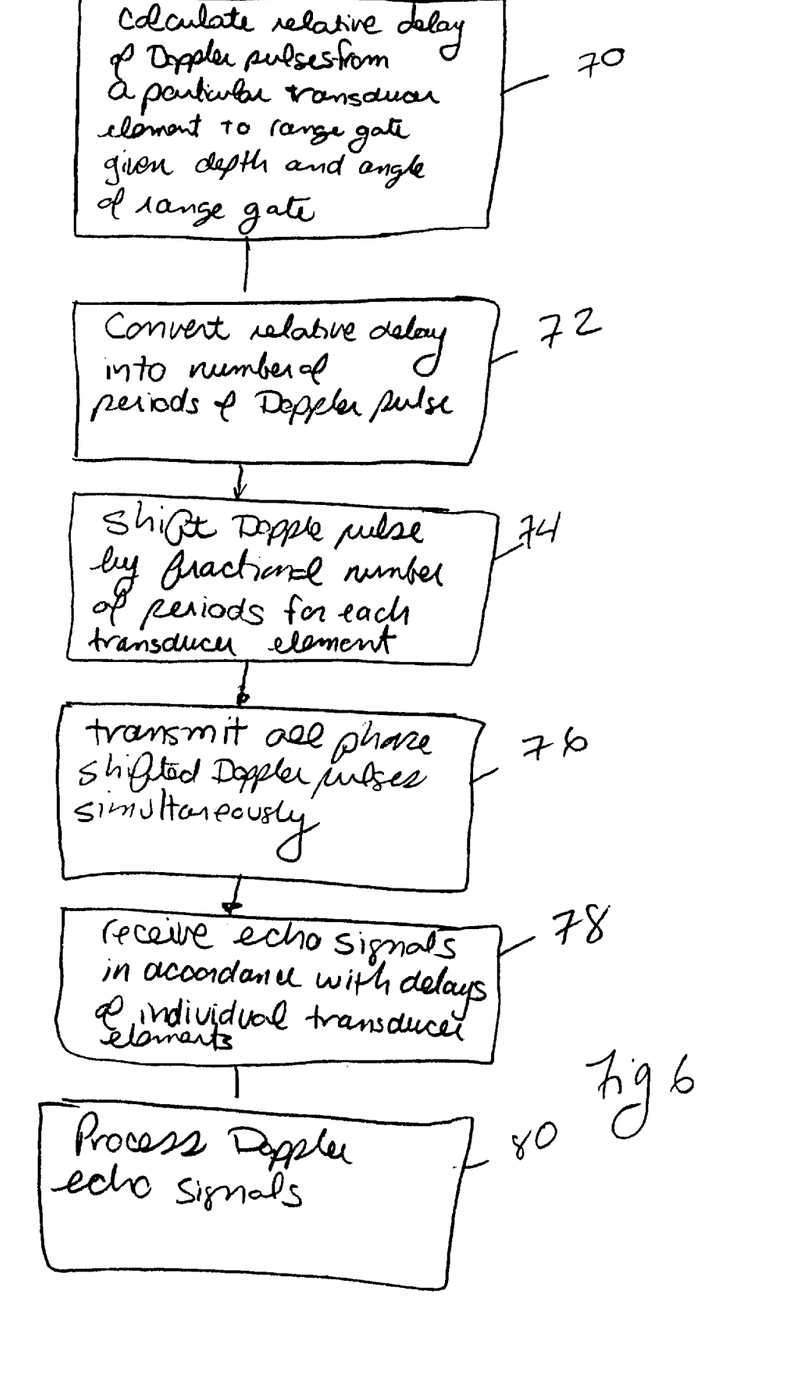
FIG. 6 is a flow chart of a method of increasing the receive time of ultrasound signals according to a second embodiment of the invention.

FIG. 6 is a flow chart of the steps performed by the second embodiment of the present invention. Beginning at a step 70, the time required to transmit an ultrasonic sound wave from each transducer element to a focal point on a transmit beam line is calculated from the user supplied angle of the beam line and depth and size of the range gate. At a step 72, the relative time delay for each transducer element is converted into a phase shift of the Doppler pulse to be transmitted relative to the pulse transmitted from the closest element. For example, if a first transducer element is positioned at 80 mm from the focal point of a combined Doppler pulse, then the delay associated with that element will be approximately 80 mm/1.54 mm/μsec or 51.94 μsec. The delay for a transducer element positioned at 75 mm from the focal point will be approximately 48.70 μsec. If the Doppler pulse transmitted from each element has a frequency of 10 MHz, then the phase difference between the pulses transmitted from the first and second elements will be 51.94–48.70 μsec=3.24 μsec mod 0.1 μsec=0.40 or 144°. At a step 74, the phase of the Doppler pulse to be transmitted from each transducer element is shifted to compensate for the varying delay times. At a step 76, each transducer element simultaneously transmits a phase-shifted Doppler pulse that compensates for the delay associated with that transducer element's position with respect to the focal point.

At a step 78, the echo signals created in response to the simultaneously transmitted Doppler pulses are received. These echo signals can be sampled at virtually any rate in order to analyze the flow of blood at the region of the focal point. At a step 80, the received echo signals are processed and displayed for the user.

Figure 7:
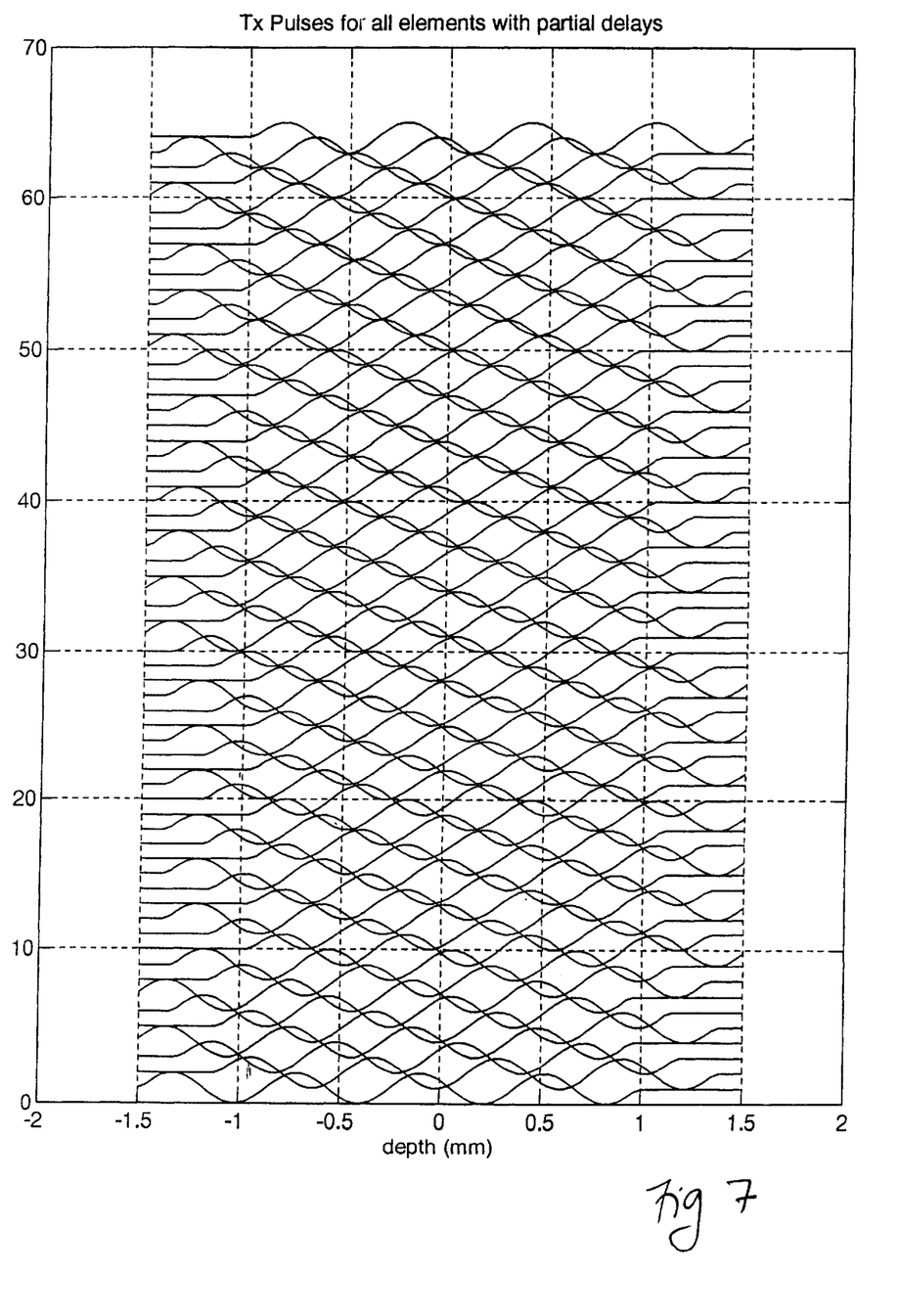
FIG. 7 illustrates a number of phase-shifted Doppler ultrasound pulses that are simultaneously transmitted from a number of transducer elements according to the method shown in FIG. 6.

FIG. 7 illustrates the simultaneous transmission of phase-shifted Doppler pulses from each transducer element. As indicated above, the phase of the Doppler ultrasound pulse that is transmitted from each transducer element is adjusted in accordance with the relative time delay associated with the distance of the transducer element to the desired focal point of the Doppler pulse.

Figure 8A:
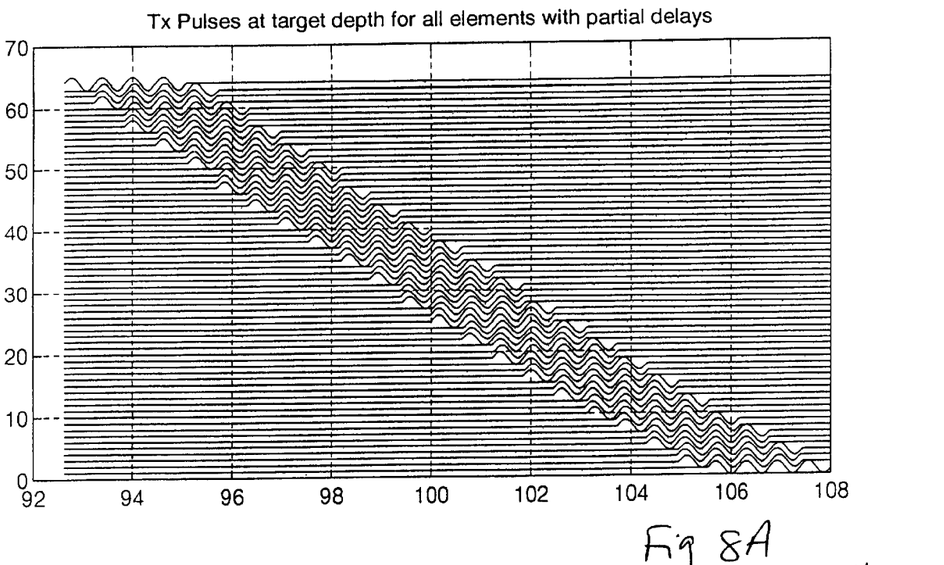
FIGS. 8A and 8B illustrate the constructive effect of the simultaneously transmitted, phase-adjusted Doppler pulses in the area of tissue defined by a range gate.
Figure 8B:
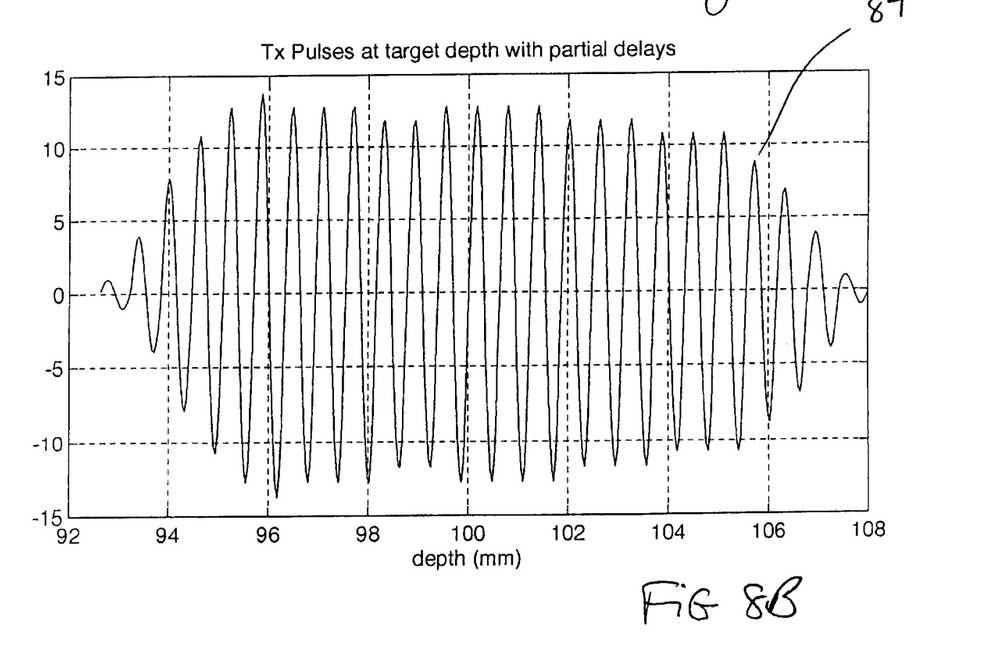

FIGS. 8A and 8B illustrate the effect of the simultaneously transmitted, phase-shifted Doppler pulses. Because each transducer element is located a varying distance from the desired focal point, the individual Doppler pulses arrive at the focal point at different times. In the example shown in FIG. 8A, the pulse transmitted by transducer element number 63 is the first to arrive at the focal point because element number 63 is the closest to the focal point. The pulse from element number 0 is the last to arrive because transducer element number 0 is the furthest from the focal point. Even though the individual Doppler pulses arrive at different times, the individual pulses arrive in-phase and therefore constructively add at the focal point. The result is a combined pulse 84 as shown in FIG. 8B. As can be seen by comparing the combined pulse 84 shown in FIG. 8B with the combined pulse 52 shown in FIG. 5B, the duration of the combined pulse 84 is greater than combined pulse 52, although its amplitude is smaller. The echo signals created in response to the combined pulse 84 are sampled at substantially any rate in order to analyze moving blood flow in the area of tissue defined by the range gate. As can be appreciated, the effect of simultaneously transmitting the phase shifted Doppler pulses is to extend the time during which echo signals can be received and therefore increase the size of the range gate.

Using the phase delays during transmission, as shown in FIGS. 7 and 8A, the resultant transmit pulse at the focal depth will be longer than the transmit time. The transmit and receive processes are reciprocal, therefore, the same principle can be applied to the receive side. By using the phase delay in receive beamforming, the received signal will cover a larger range gate size than what the receive time gives.

FIG. 8B can be seen as the signal in the range gate. It can be decomposed into shorter sections for each channel as shown in FIG. 8A. If phase delays are applied to each of the receive channels, the channels will receive signals as shown in FIG. 7. In the case shown, the receive time is only four cycles per channel, but the total received signal covers about 24 cycles.

Figure 9:
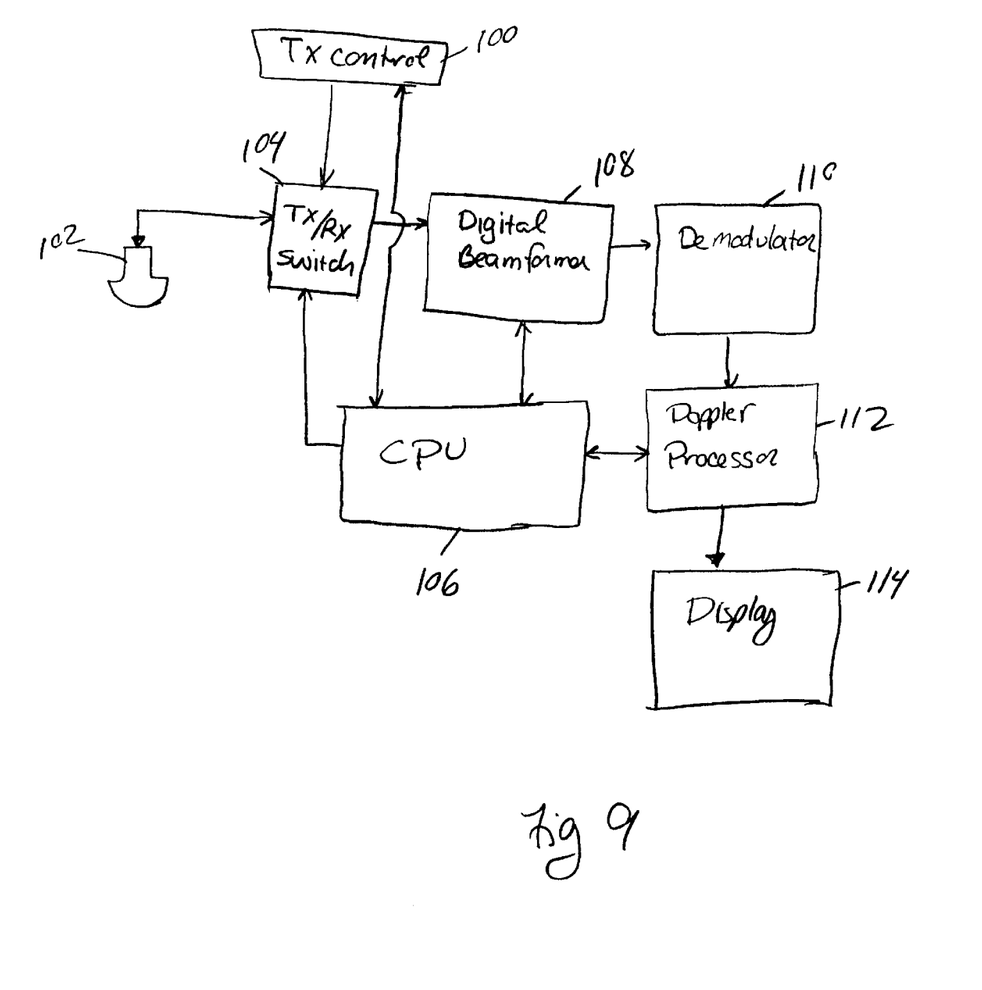
FIG. 9 is a block diagram of an ultrasound system that operates according to the present invention.

FIG. 9 is a block diagram of an ultrasound system that operates in accordance with the present invention. The system includes a transmit control 100 that supplies the Doppler pulses to be delivered to transducer 102 through a transmit/receive switch 104.

A CPU 106 directs the transmit control 100 to produce the long Doppler pulse as discussed in connection with FIG. 2 or the phase shifted Doppler pulses as discussed in connection with FIGS. 6 and 7 and to deliver these pulses to the transducer at the appropriate times.

Echo signals received by the transducer 102 are routed through the transmit/receive switch 104 to a digital beamformer 108 that focuses the received echoes in the area of tissue defined by the position of the range gate. From the beamformer 108, the echo signals are demodulated by a demodulator 110. From the demodulator 110, the echo signals are supplied to a Doppler processor 112 that determines the direction and velocity of the moving blood flow in the area of tissue defined by the range gate.

The output of the Doppler processor depends on the mode in which the ultrasound system is operating. The output may be a graph, or color enhancement that overlays a B-mode image. The output of the Doppler processor is supplied to a display 114 to be seen by a physician or sonographer.

As can be seen from the above, the present invention operates to increase the receive time of ultrasound echo signals created in response to Doppler pulses, such that the echoes can be sampled at substantially any rate in order to more accurately analyze fast moving blood flow at greater depths or with greater range gate size.

The embodiments of the invention in which an exclusive property or privilege is claimed are defined as follows:

1. A method of producing Doppler ultrasound data from an area of tissue defined by a range gate, comprising:
   transmitting a Doppler pulse having a duration substantially equal to the time required for an ultrasonic sound wave to travel from a transducer to a top of a range gate and back;
   receiving echo signals created in response to the Doppler pulse transmitted;
   sampling the received echo signals at a desired rate; and
   using the sampled echo signals to analyze moving blood flow in the area of tissue defined by the range gate.

2. The method of claim 1, wherein the step of receiving Doppler echo signals comprises:
   receiving the echo signals for a period of time substantially equal to a time required for an ultrasonic sound wave to travel from the transducer to a bottom of the range gate and back.

3. A method of producing Doppler ultrasound data from an area of tissue defined by a range gate, comprising:
   determining a time required for an ultrasonic sound wave to travel between a number of individual transducer elements of an ultrasound transducer and a focal point of a Doppler pulse;
   shifting the phase of a Doppler pulse to be transmitted from each transducer element based on the times determined;
   simultaneously transmitting a phase-shifted Doppler pulse from each transducer element; and
   sampling echo signals created in the area of tissue defined by the range gate in response to the simultaneously transmitted, phase-shifted Doppler pulses.

4. The method of claim 3, wherein the phase of the Doppler pulses is shifted such that the Doppler pulses add coherently in the area of tissue defined by the range gate.

5. A Doppler ultrasound system, comprising:
   a transducer that transmits Doppler pulses into tissue and generates electronic echo signals in response to received echoes;
   a transmit control that supplies the Doppler pulses to the transducer;
   a central processing unit that directs the transmit control to supply the Doppler pulses to the transducer such that a period of time during which the transducer receives the echoes responsive to a position shorter than the transmit time is greater than a period of time during which the transducer is transmitting Doppler pulses into the tissue;

a digital beamformer controlled by the central processing unit that focuses the electronic echo signals received from an area of tissue defined by a range gate; and a Doppler processor that receives the focused echo signals and determines the direction and velocity of moving blood flow in the area of tissue defined by the range gate.

6. The Doppler ultrasound system of claim 5, wherein the central processing unit increases the receive time of the echoes with respect to the transmit time of the Doppler pulses by:

directing the transmit control to deliver a Doppler pulse to the transducer that has a duration substantially equal to the time required for an ultrasonic sound wave to travel from the transducer to a top of a range gate and back; and directing the digital beamformer to receive the electronic echo signals for a time substantially equal to the time required for an ultrasonic sound wave to travel from the transducer to a bottom of a range gate and back.

7. The Doppler ultrasound system of claim 5, wherein the central processing unit increases the receive time of the echoes with respect to the transmit time of the Doppler pulses by:

directing the transmit control to supply phase shifted Doppler pulses to a number of individual transducer elements for simultaneous transmission, wherein the phase shift of each Doppler pulse is determined by a transducer element's distance from the focal point of the Doppler pulses.

* * * * *